(12) United States Patent
Shanley, IV

(10) Patent No.: US 11,318,033 B2
(45) Date of Patent: May 3, 2022

(54) COMPLIANT ELBOW BRACE CONFIGURATIONS

(71) Applicant: John Francis Shanley, IV, Urbana, IL (US)

(72) Inventor: John Francis Shanley, IV, Urbana, IL (US)

(73) Assignee: Phase 3 Projects, LLC, Emerald Hills, CA (US)

( * ) Notice: Subject to any disclaimer, the term of this patent is extended or adjusted under 35 U.S.C. 154(b) by 364 days.

(21) Appl. No.: 15/372,250

(22) Filed: Dec. 7, 2016

(65) Prior Publication Data

US 2017/0181879 A1    Jun. 29, 2017

Related U.S. Application Data

(60) Provisional application No. 62/264,193, filed on Dec. 7, 2015.

(51) Int. Cl.
*A61F 5/01*    (2006.01)

(52) U.S. Cl.
CPC ............ *A61F 5/0118* (2013.01); *A61F 5/013* (2013.01); *A61F 5/0106* (2013.01);
(Continued)

(58) Field of Classification Search
CPC ...... A61F 5/0102; A61F 5/0118; A61F 5/013; A61F 5/0123; A61F 5/01; A61F 5/0104; A61F 5/05; A61F 5/058; A61F 5/05841; A61F 5/0585; A61F 5/05858; A61F 5/37; A61F 5/3723; A61F 5/373; A61F 2005/0146; A61F 2005/0151; A61F 2005/165; A61F 5/0106; A61H 1/0274; A61H 1/0277; A61H 1/024; A61H 1/0237–0262; A61H 3/00
(Continued)

(56) References Cited

U.S. PATENT DOCUMENTS 5,031,606 A  *  7/1991  Ring, Sr. ................. A61F 5/013
                                                    602/16
6,031,606 A  *  2/2000  Bayer ...................... G01C 1/04
                                                    250/203.2

(Continued)

OTHER PUBLICATIONS

Fichera et al : "A Numerical Model to Analyze the Dynamic Response of a Vehicle to Variations in Torque Transmitted by the Drive-line"; SAE International Journal of Passenger Cars—Mechanical Systems—Jan. 2001 (Year: 2001).*

*Primary Examiner* — Caitlin A Carreiro
(74) *Attorney, Agent, or Firm* — Vista IP Law Group, LLP

(57) ABSTRACT

One embodiment is directed to a brace for limiting motion of a joint of an appendage of that is interposed between a first appendage portion and a second appendage portion of a patient, comprising: an upper member removably coupleable to the first appendage portion, the upper member having proximal and distal ends; and a lower member removably coupleable to the second appendage portion, the lower member having proximal and distal ends; wherein the distal end of the upper member and proximal end of the lower member are coupled to form a movable joint that is substantially alignable with the joint of the patient, such that when the patient attempts to move his appendage and associated joint, motion is resisted at this joint in a nonlinear fashion.

9 Claims, 3 Drawing Sheets

(52) U.S. Cl.
CPC .............. *A61F 5/0123* (2013.01); *A61F 5/01* (2013.01); *A61F 5/0102* (2013.01); *A61F 5/0104* (2013.01)

(58) Field of Classification Search
USPC .................... 602/16, 20, 26, 5, 23; 482/124; 128/878, 881, 882; 601/33, 34
See application file for complete search history.

(56) References Cited

U.S. PATENT DOCUMENTS

| | | | |
|---|---|---|---|
| 2013/0075966 A1* | 3/2013 | Carvey | F16F 1/10 267/156 |
| 2013/0190669 A1* | 7/2013 | Rokosz | A61F 5/0125 602/16 |

\* cited by examiner

COMPLIANT ELBOW BRACE CONFIGURATIONS

RELATED APPLICATION DATA

The present application claims the benefit under 35 U.S.C. § 119 to U.S. provisional patent application Ser. No. 62/264,193 filed Dec. 7, 2015. The foregoing application is hereby incorporated by reference into the present application in its entirety.

FIELD OF THE INVENTION

The present invention is related to orthopaedic devices, and specifically to brace configurations for joints of the human skeleton which feature compliant motion-constraining elements.

BACKGROUND

There is a large market in the U.S. and other countries for braces of various configurations to stabilize joints of the body—in postoperative scenarios, injury prevention scenarios, and the like. Perhaps the most common are knee joint braces, often configured to add stability to an injured or recovering cruciate ligament. Injuries to the human elbow are also somewhat common, and elbow joint braces have been created to stabilize the elbow joint to prevent injury and/or facilitate recovery from a surgery or injury. One type of elbow brace that has been used clinically is one which is designed to enforce a flexion range of motion (or "ROM") reduction or contracture at the elbow joint. For example, in certain scenarios, such as in the rehabilitation after surgical intervention of the ulnar collateral ligament of the elbow, it is desirable clinically to maintain the patient's range of motion to a confined range—one less than is typically capable for the patient; this may be accomplished with a ROM-reduction brace that typically has one portion removably coupled to the upper arm, such as by a strap, another portion coupled to the forearm, such as by another strap, and a joint between the first portion and second portion which limits the rotation of the elbow joint—typically by one or more rotational motion "stops" built into the brace (such as pins, the positions of which may be adjusted to prescribe a particular range of motion) which prevent rotation beyond a particular point. One of the challenges with such configurations is that when the patient's arm is being rotated toward one of the mechanical stops and then encounters the rotational limitation provided by such stop, there may be an uncomfortably large deceleration of the patient's forearm relative to the upper arm, which may cause pain or disruption to the healing joint that is the subject of the protection/stabilization from the brace. There is a need for a joint ROM-reducing brace configuration which functions to reduce the range of motion to a prescribed range, but also has compliant features to prevent abrupt deceleration when the envelope of the prescribed range of motion is reached by the user.

SUMMARY OF THE INVENTION

One embodiment is directed to a brace for limiting motion of a joint of an appendage of that is interposed between a first appendage portion and a second appendage portion of a patient, comprising: an upper member removably coupleable to the first appendage portion, the upper member having proximal and distal ends; and a lower member removably coupleable to the second appendage portion, the lower member having proximal and distal ends; wherein the distal end of the upper member and proximal end of the lower member are coupled to form a movable joint that is substantially alignable with the joint of the patient, such that when the patient attempts to move his appendage and associated joint, motion is resisted at this joint in a nonlinear fashion.

DETAILED DESCRIPTION

Figure 1:
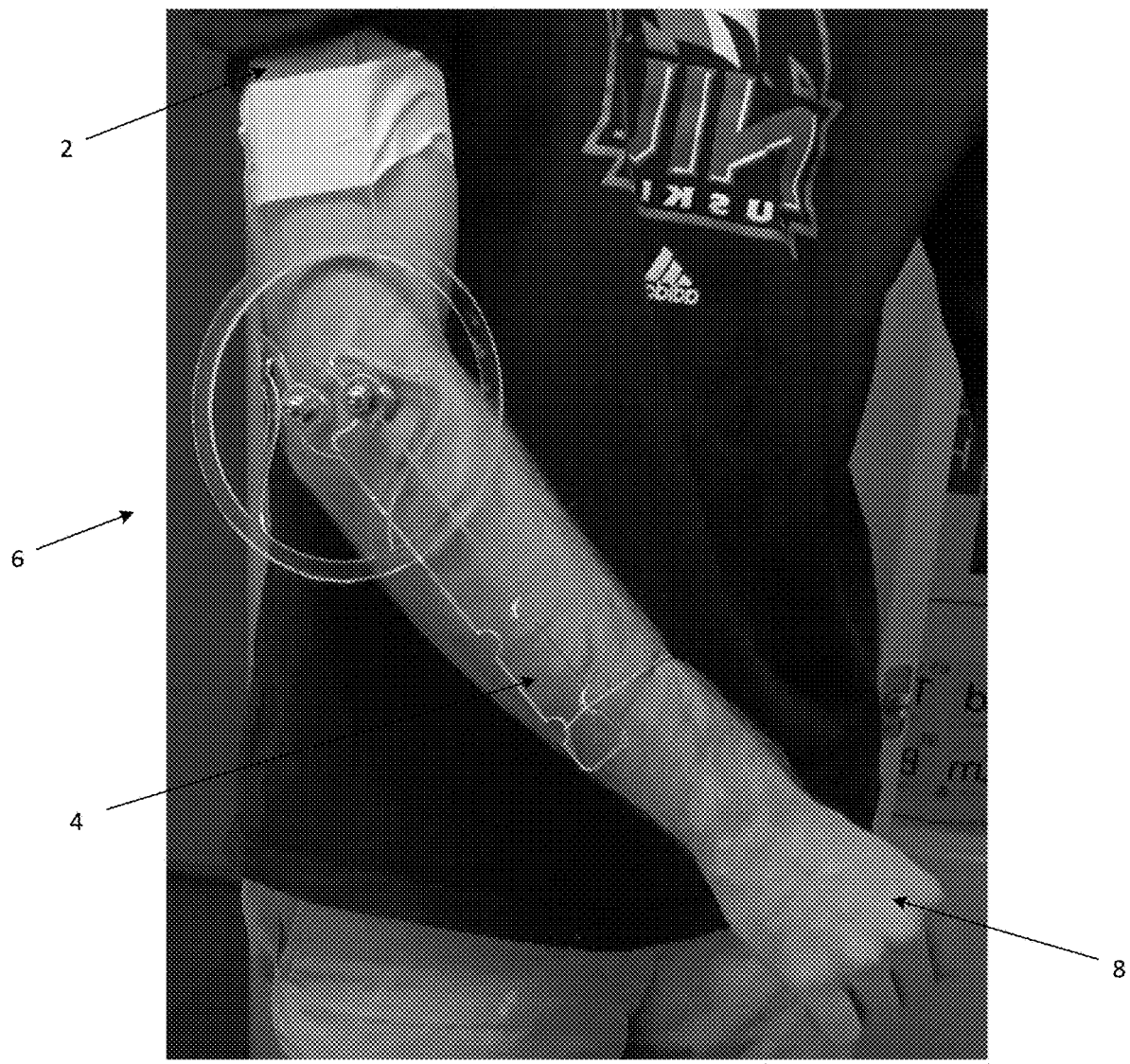
FIG. 1 illustrates aspects of a compliant arm brace configuration in accordance with the present invention, installed on a patient's arm.
Figure 2:
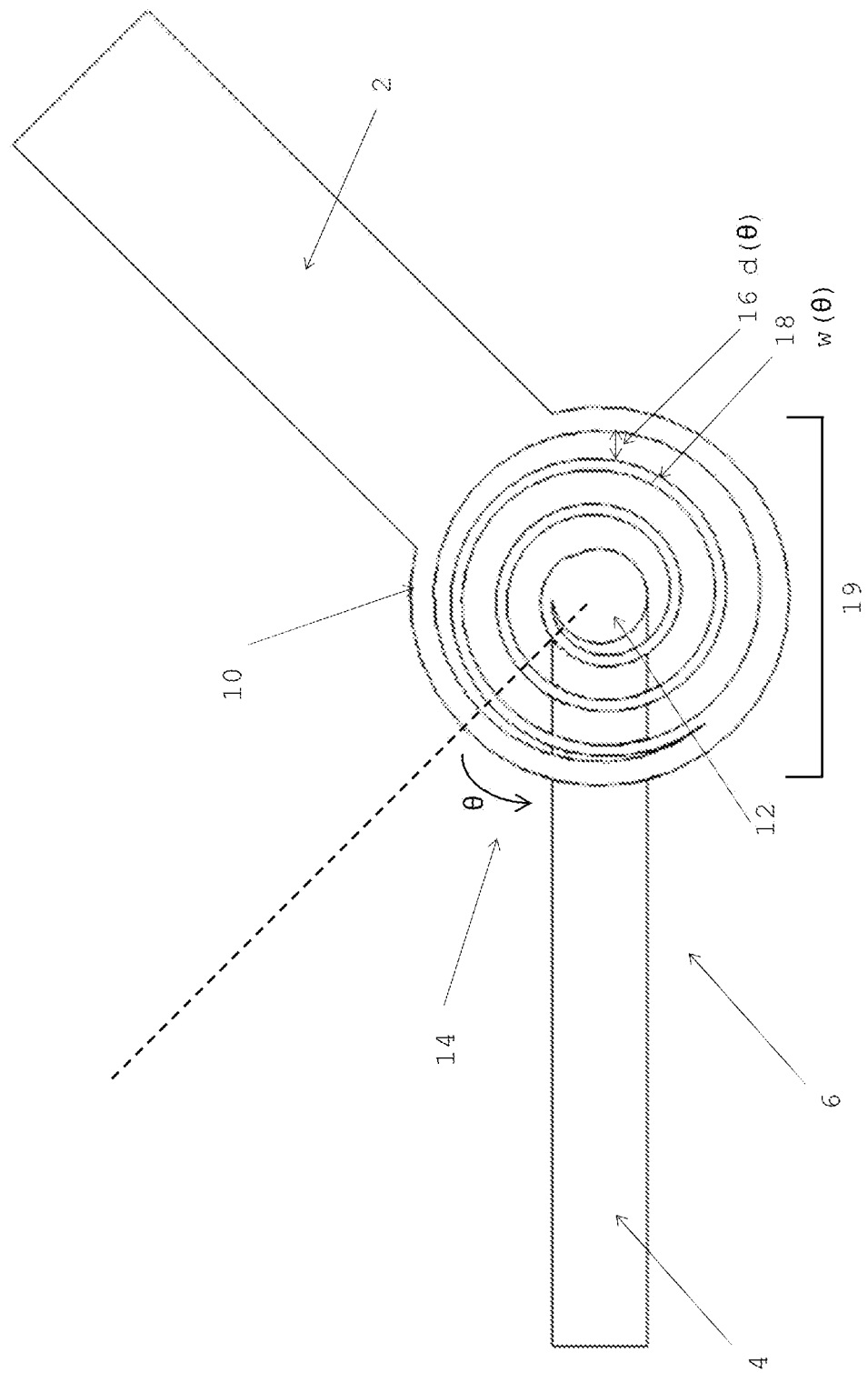
FIG. 2 illustrates aspects of a compliant arm brace configuration in accordance with the present invention.
Figure 3:
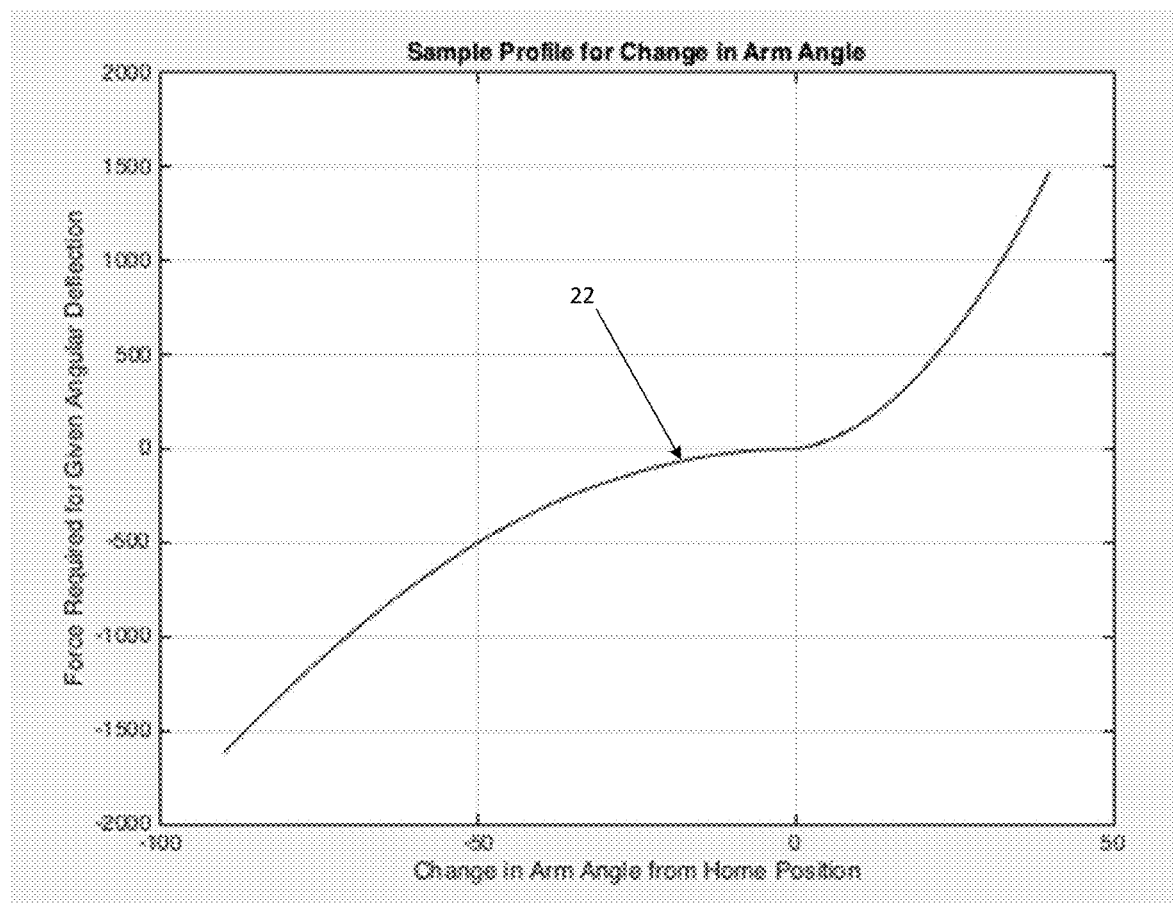
FIG. 3 illustrates aspects of a nonlinear force profile suitable for a compliant arm brace configuration in accordance with the present invention.
Figure 3:
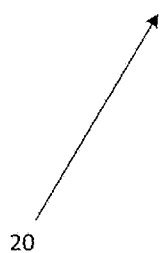

Referring to FIG. 1 and FIG. 2, various configurations for a compliant elbow brace (6) configuration are depicted. In one embodiment, the brace configuration comprises a nonlinear torsion spring (19) that minimizes the impulse of reaching the end of the rotational travel length. In one basic embodiment, two members are connected to the torsional spring (19), one (the "upper member", 2) removably coupled to the upper appendage (8) of the user at a location above the elbow, the other (the "lower member", 4) removably coupled to the upper appendage (8) of the user at a location below the elbow. There may be a "home position" defined as the angle that the two arms (2, 4) fixed to the spring (19) make while at rest. In one embodiment, to move away from this home position, a torque is required by the user. One key concept of one embodiment is that as the user gets further and further from the home position, the brace (6) is configured such that it takes a larger torque to move one unit of rotation (demonstrated conceptually in the plot (20) in FIG. 3, wherein the force required for a given angular deflection is configured to vary nonlinearly (22) relative to change in arm angle, or elbow flexion rotation angle, from the home position). Referring again to this diagram (20) in FIG. 3, the rest position is shown as zero—in other words, if one adds this angle to the angle of the home position (which varies based on the type of injury), one gets the torque required to hold a certain angle between the forearm and upper arm using the device. As described above, it is desired that the device serve the purpose of protecting an elbow joint without the impulse shock that can occur using current technology brace configurations. With the configurations described herein, a rotational range of motion would be limited with a cushioning force as opposed to a hard cut-off, decreasing user discomfort and further protecting the joint. With such configurations, it is true that a torque would be needed to move the joint at all, but this issue can be mitigated by making the spring stiffness very small near the home position.

As noted above, FIG. 1 illustrates aspects of one embodiment of a prototype brace (6) configuration with upper (2) and lower (4) members coupled to a user's arm (8) and a compliant ROM-reducing configuration therebetween. FIG. 2 illustrates another prototype brace (6) configuration with upper (2) and lower (4) members being configured to be removably coupleable to upper arm and forearm positions of the user's upper appendage (8), respectively, with a compliant ROM-reducing configuration therebetween. In such configuration, the lower member (4) is fixedly coupled to the inner disk member (12), and the upper member (2) is fixedly coupled to the outer ring member (10) as illustrated in FIG. 2. An angular position, theta (14), is shown in FIG. 2, and between the outer ring (10) and inner disk (12), the radial spacing (d(theta)—16) and radial width (w(theta)—18) may be varied with rotational position to map in a functional equation for rotational load resistance versus rotational deflection between the upper member and lower member. One advantage to providing such functionality with compliant mechanisms is that compliant mechanisms can be created from a minimal number of parts (some are single-part compliance members), and consequently can be significantly cheaper to produce compared to larger, more intricate designs. These concepts may be utilized in brace mechanisms for other joints, most immediately to the human knee, due to inherent structural similarities.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject systems. The methods may comprise the act of providing such a suitable system. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A brace for limiting motion of a joint of an appendage that is interposed between a first appendage portion and a second appendage portion of a patient, the brace consisting of:

an upper member configured to removably couple to the first appendage portion of the patient, the upper member having proximal and distal ends;

a lower member configured to removably couple to the second appendage portion of the patient, the lower member having proximal and distal ends; and a single non-linear torsion spring having an inner disk member disposed at a center of the non-linear torsion spring and an outer ring member coupled by a spiral member to the inner disk member, wherein each successive coil of the spiral member is defined by a radial width and is separated from adjacent coils of the spiral member by a radial spacing, wherein the radial width and radial spacing are varied with rotational position to map rotational load resistance versus rotational deflection between the upper member and the lower member, the non-linear torsion spring being configured to provide first and second resistive forces against relative movement of the upper and lower members in respective first and second directions from a home position, wherein the first and second directions are different from each other, wherein each of the first and second resistive forces increases in a nonlinear fashion relative to a change in angle from the home position along respective first and second, curves of a nonlinear force profile where the first and second curves are asymmetrical along an X-axis representing an angular change from the home position and a Y-axis representing a force required for angular deflection, and wherein the distal end of the upper member is fixedly coupled to the outer ring member and the proximal end of the lower member is fixedly coupled to the inner disk member to form a one piece structure having a movable joint configured to be aligned with the joint of the patient, such that when the patient attempts to move the appendage and associated joint, motion is resisted at the joint by the first or second resistive forces that increase in a nonlinear fashion as the appendage is moved away from the home position in the first direction or the second direction, wherein the brace is configured such that during use, as the appendage is moved further away from the home position, a larger torque is required to move one unit of rotation to prevent abrupt deceleration when an end of a prescribed range of motion is reached.

2. The brace of claim 1, wherein the upper member is configured to be removably coupled to a thigh portion of a leg of the patient.

3. The brace of claim 2, wherein the lower member is configured to be removably coupled to a lower leg portion of a leg of the patient.

4. The brace of claim 1, wherein the non-linear torsion spring is configured to limit a range of motion by compliantly deforming to resist motion at the associated joint of the patient.

5. The brace of claim 1, wherein the upper member is configured to be removably coupled to an upper arm portion of an arm of the patient.

6. The brace of claim 5, wherein the lower member is configured to be removably coupled to a forearm portion of an arm of the patient.

7. The brace of claim 1, wherein the non-linear torsion spring is configured to minimize an impulse of reaching an end of a rotational travel length.

8. The brace of claim 1, wherein the brace is configured such that in the home position, the non-linear torsion spring biases the upper and lower members.

9. The brace of claim 1, wherein the first resistive force increases at a different absolute rate from the home position compared to the second resistive force.

* * * * *